(12) United States Patent
Szczepek et al.

(10) Patent No.: US 7,674,901 B2
(45) Date of Patent: Mar. 9, 2010

(54) PROCESS FOR PREPARATION OF IMATINIB BASE

(75) Inventors: Wojciech Szczepek, Warsaw (PL);
Wojciech Luniewski, Warsaw (PL);
Lukasz Kaczmarek, Warsaw (PL);
Bogdan Zagrodzki, Warsaw (PL);
Dorota Samson-Lazinska, Warsaw (PL); Wieslaw Szelejewski, Warsaw (PL); Maciej Skarzynski, Warsaw (PL)

(73) Assignee: Instytut Farmaceutyczny, Warsaw (PL)

( * ) Notice: Subject to any disclaimer, the term of this patent is extended or adjusted under 35 U.S.C. 154(b) by 0 days.

(21) Appl. No.: 11/813,212

(22) PCT Filed: Dec. 30, 2005

(86) PCT No.: PCT/PL2005/000088

§ 371 (c)(1),
(2), (4) Date: Nov. 21, 2007

(87) PCT Pub. No.: WO2006/071130

PCT Pub. Date: Jul. 6, 2006

(65) Prior Publication Data

US 2008/0194819 A1 Aug. 14, 2008

(30) Foreign Application Priority Data

Dec. 30, 2004 (PL) ................... P.372016
Aug. 19, 2005 (PL) ................... P.376691
Nov. 8, 2005 (PL) ................... P.377984

(51) Int. Cl.
*C07D 419/00* (2006.01)
(52) U.S. Cl. ................ 544/331; 544/359; 546/274.1
(58) Field of Classification Search .............. 544/331, 544/359; 546/274.1
See application file for complete search history.

(56) References Cited

U.S. PATENT DOCUMENTS 6,075,018 A * 6/2000 Vago et al. ................ 514/221

OTHER PUBLICATIONS

Szakacs, et al. J. Med. Chem., 48(1), 2005, 249-255.*
Gubicza, et al. J. Biotechnol., 84, 2000, 193-196.*

* cited by examiner

*Primary Examiner*—James O Wilson
*Assistant Examiner*—Douglas M Willis
(74) *Attorney, Agent, or Firm*—Matthias Scholl, PC; Matthias Scholl

(57) ABSTRACT

An improved process for the preparation of imatinib base and its pharmaceutically acceptable acid addition salts by (a) reacting 2-methyl-5-nitroaniline with cyanamide in the presence of hydrochloric acid to obtain 1-(2-methyl-5-nitrophenyl)guanidine hydrochloride; (b) converting 1-(2-methyl-5-nitrophenyl)guanidine hydrochloride to 1-(2-methyl-5-nitrophenyl)guanidine nitrate; (c) condensing 3-acetylpyridine with N,N-dimethylformamide dimethyl acetal to obtain 3-(dimethylamino)-1-(3-pyridinyl)-prop-2-en-1-one; (d) reacting 3-(dimethylamino)-1-(3-pyridinyl)-prop-2-en-1-one with 1-(2-methyl-5-nitrophenyl)guanidine nitrate to obtain N-(5-nitro-2-methylphenyl)-4-(3-pyridinyl)-2-pyrimidineamine; (e) reducing N-(5-nitro-2-methylphenyl)-4-(3-pyridinyl)-2-pyrimidineamine using hydrazine in the presence of Raney nickel to obtain N-(5-amino-2-methylphenyl)-4-(3-pyridinyl)-2-pyrimidine-amine; (f) condensing N-(5-amino-2-methylphenyl)-4-(3-pyridinyl)-2-pyrimidine-amine with 4-chloromethylbenzoyl chloride in the presence of an inorganic base to obtain 4-(chloromethyl)-N-(4-methyl-3-(4-(pyridin-3-yl)pyrimidin-2-ylamino)phenyl)benzamide; and (g) condensing 4-(chloromethyl)-N-(4-methyl-3-(4-(pyridin-3-yl)pyrimidin-2-ylamino)phenyl)benzamide with an excess of N-methylpiperazine to obtain imatinib base; and adding water or a mixture of water and an organic solvent; and isolating said imatinib base. The process allows for using simple starting materials, while simultaneously avoiding a laborious isolation and purification of intermediates and the final product, thereby facilitating scale-up.

18 Claims, No Drawings

PROCESS FOR PREPARATION OF IMATINIB BASE

CROSS-REFERENCE TO RELATED APPLICATIONS

This is a National Stage Application of International Patent Application No. PCT/PL 2005/000088, with an international filing date of Dec. 30, 2005, which is based on Polish Patent Applications Nos. P.372016, filed Dec. 30, 2004, P.376691, filed Aug. 19, 2005, and P.377984, filed Nov. 8, 2005. The contents of all of these specifications, including subsequent amendments thereto, are incorporated herein by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The invention relates to an improved process for the preparation of imatinib base and the pharmaceutically acceptable acid addition salts thereof. Further, the invention relates to processes for preparing intermediates in the synthesis of imatinib base and the pharmaceutically acceptable acid addition salts thereof.

2. Description of the Related Art

Imatinib, N-(4-methyl-3-(4-(pyridin-3-yl)pyrimidin-2-ylamino)phenyl)-4-((4-methylpiperazin-1-yl)methyl)benzamide, also referred to as imatinib base, is a selective inhibitor of tyrosine kinase, disclosed in EP 0564409 A1, and represented by the structural formula:

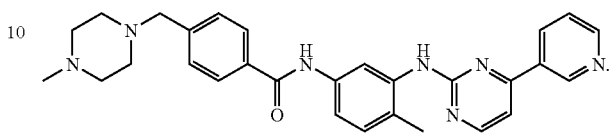

Methanesulfonic acid addition salt of imatinib is an active ingredient of oral compositions useful in the treatment of patients with Philadelphia chromosome positive chronic myeloid leukemia and with Kit-positive unresectable and/or metastatic malignant gastrointestinal stromal tumors.

Three basic synthetic pathways for preparation of imatinib base are known in the art (methods A-C).

Scheme 1 illustrates a first synthetic pathway for preparation of imatinib base, referred to herein as "Method A". This method is known from EP 0564409 A1 and WO 2004/074502, and comprises the condensation of two chemical moieties, N-(5-amino-2-methylphenyl)-4-(3-pyridinyl)-2-pyrimidineamine and 4-(4-methylpiperazinelmethyl)benzoyl chloride.

Scheme 2 illustrates a second synthetic pathway for preparation of imatinib base, referred to herein as "Method B." This method is known from WO 03/066613, and comprises condensation of 4-(3-pyridinyl)-2-pyrimidineamine, or a precursor thereof, with N-(3-bromo-4-methylphenyl)-4-(4-methylpiperazin-1-ylmethyl)-benzamide.

Method A

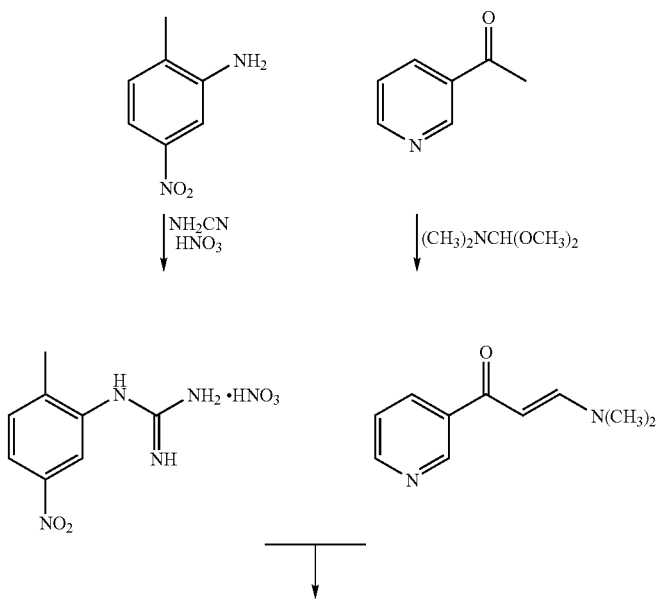

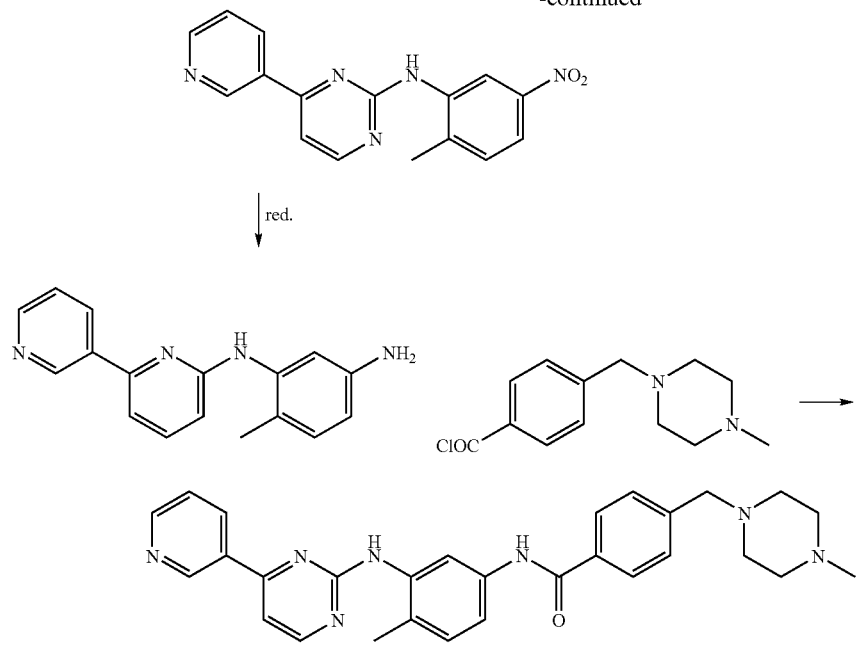
Method B
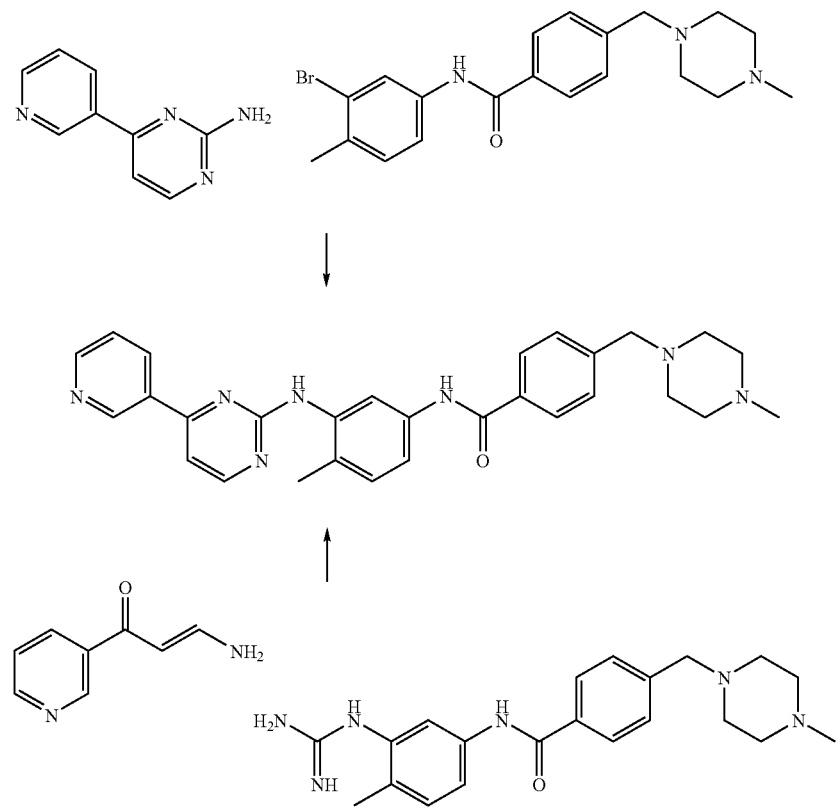

Scheme 3 illustrates a third synthetic pathway for preparation of imatinib base, referred to herein as "Method C." This method is described in WO 2004/108699 and in J. Med. Chem. 2005, 48(1), 249-255, and comprises the condensation of 4-methyl-N-3-(4-pyridin-3-yl-pyrimidin-2-yl)benzene-1,3-diamine with 4-chloromethylbenzoyl chloride to yield 4-chloromethyl-N-(4-methyl-3-((4-pyridin-3-yl)-pyrimidin-2-ylamino)-phenyl)-benzamide, followed by the reaction of 4-chloromethyl-N-(4-methyl-3-((4-pyridin-3-yl)-pyrimidin-2-ylamino)-phenyl)-benzamide with N-methylpiperazine.

Method C

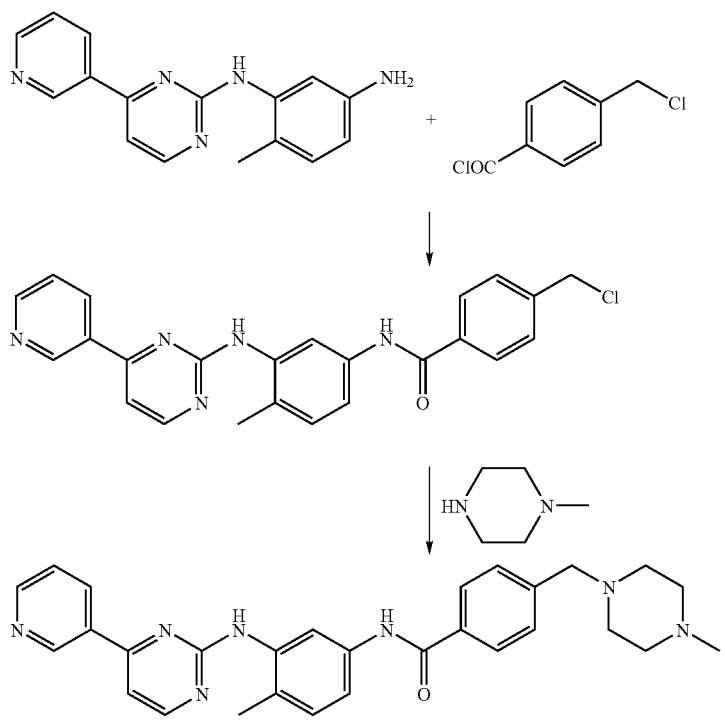

Scheme 3

The methods known in the art are characterized by inconveniences which make the synthesis troublesome and difficult to scale up.

The first key intermediate in the synthesis of imatinib by Methods A and C is the N-(5-nitro-2-methylphenyl)-4-(3-pyridinyl)-2-pyrimidineamine that, according to EP 0564409 A1, is obtained by condensation of 1-(2-methyl-5-nitrophenyl)guanidine with 3-(dimethylamino)-1-(3-pyridinyl)-prop-2-en-1-one.

3-(Dimethylamino)-1-(3-pyridinyl)-prop-2-en-1-one is obtained by refluxing a mixture of 3-acetylpyridine with a molar excess (1.09-4.7 equivalents) of N,N-dimethylformamide dimethyl acetal for 6-16 hours, and isolating the resultant product by concentrating the reaction mixture in vacuo, treating the residue with hexane and filtering the formed crystals (See, U.S. Pat. No. 4,281,000, EP 0025819 B1, and U.S. Pat. No. 4,374,988).

Usually, the crude 3-(dimethylamino)-1-(3-pyridinyl)-prop-2-en-1-one is purified by direct recrystallization from a suitable solvent, or by dissolving in methylene chloride, filtering through a layer of magnesium silicate, and recrystallization. Alternatively, the purified product is isolated by concentrating the reaction mixture in vacuo, dissolving the residue in methylene chloride and filtering the obtained solution through a layer of magnesium silicate followed by recrystallization.

Unfortunately, 3-(dimethylamino)-1-(3-pyridinyl)-prop-2-en-1-one is easily soluble in organic solvents as well as in water, and therefore the yield of the product isolated by recrystallization is poor (50-66%) compared to that of the solid crude product (85-89%). For example, per U.S. Pat. No. 4,281,000, the yield of 3-(dimethylamino)-1-(3-pyridinyl)-prop-2-en-1-one obtained by the reaction of 3-acetylpyridine with 1.09 equivalent of N,N-dimethylformamide dimethyl acetal followed by recrystallization of the crude product is only 50% (Example 1).

Another cause of poor yield of 3-(dimethylamino)-1-(3-pyridinyl)-prop-2-en-1-one may be an incomplete conversion of 3-acetylpyridine.

According to EP 0233461 B1 and EP 0564409 A1, the other key reagent in the synthesis of imatinib by Methods A and C, 1-(2-methyl-5-nitrophenyl)guanidine, can be obtained by heating 2-methyl-5-nitroaniline in the presence of an aqueous solution of cyanamide and, if necessary, an acid that would be a source of appropriate anion, for example, in the presence of a concentrated nitric acid. The resulting product is isolated from the reaction mixture in a crystalline form.

In EP 0564409 A1, the reaction of 1-(2-methyl-5-nitrophenyl)guanidine with 3-(dimethylamino)-1-(3-pyridinyl)-prop-2-en-1-one is carried out by a prolonged heating (6-48 hours) of the reagents in a neutral solvent, in the presence of an appropriate base, if necessary. The yield of N-(5-nitro-2-methylphenyl)-4-(3-pyridinyl)-2-pyrimidineamine did not exceed 75% according to a procedure disclosed in the experimental section of EP 0564409.

The prior art methods for preparing N-(5-nitro-2-methylphenyl)-4-(3-pyridinyl)-2-pyrimidineamine consist of many steps, are time-consuming and require purification of intermediates at subsequent steps of the synthesis which additionally decreases the total yield of the product.

Both methods, A and C, require the reduction of the nitro compound, N-(5-nitro-2-methylphenyl)-4-(3-pyridinyl)-2-pyrimidineamine to N-(5-amino-2-methylphenyl)-4-(3-pyridinyl)-2-pyrimidineamine.

In EP 0564409 A1, the reduction of a nitro group to an amino derivative in N-(substituted nitrophenyl)-4-(3-pyridinyl)-2-pyrimidineamines is carried out at room temperature and under ambient pressure of hydrogen in the presence of palladium on a solid support as a catalyst (i) for 6.5 hours in ethyl acetate (w/10% Pd/C), or (ii) for 21 hours in tetrahydrofuran (w/5% Pd/C). The yield of the product has not been disclosed in any of the examples.

The reduction of N-(5-nitro-2-methylphenyl)-4-(3-pyridinyl)-2-pyrimidineamine to N-(5-amino-2-methylphenyl)-4-(3-pyridinyl)-2-pyrimidineamine, described in WO 2004/074502 and WO 2004/108699, is carried out using tin(II) chloride—$SnCl_2$.

According to WO 2004/074502, the reaction with tin(II) chloride is carried out in tetrahydrofuran at 60° C. for 4 hours or in a mixture of water and concentrated hydrochloric acid at 50° C. for 2 hours. The yield of N-(5-amino-2-methylphenyl)-4-(3-pyridinyl)-2-pyrimidineamine, obtained after recrystallization from ethyl acetate, has not been given in the provided examples. However, in the description of this application the authors have disclosed that the yield was 65-70%. Hence, the yield was higher than that obtained in the reconstructed examples of EP 0564409, in which, according to the authors of WO 2004/074502, the yields are approximately 40-45%. Also, purity of the product was higher, and consumption of organic solvents was lower.

In WO 2004/108699, reduction with the use of tin(II) chloride was carried out in concentrated hydrochloric acid at temperature 0-5° C. for 3-4 hours and then at 25-35° C. for 1.5 hour to afford, after recrystallization from ethyl acetate, the yield of N-(5-amino-2-methylphenyl)-4-(3-pyridinyl)-2-pyrimidineamine was 60-64.5%.

A publication in the J. Med. Chem., 2005, 48(1), 249-255, describes the reduction of N-(5-nitro-2-methylphenyl)-4-(3-pyridinyl)-2-pyrimidineamine using $SnCl_2.H_2O$ in a concentrated hydrochloric acid at room temperature for 30 min, where the yield of the amine after recrystallization of the crude product from methylene chloride was 81%. The yield is higher compared to that reported in WO 2004/074 502 and WO 2004/108 699.

It is common knowledge that a reduction of aromatic nitro compounds to the corresponding amines can be accomplished:
- by using metals such as zinc (Zn), tin (Sn), iron (Fe), etc., in an acidic medium (e.g., hydrochloric acid), or by using tin (II) chloride in an acidic medium (e.g., hydrochloric acid) or alternatively, by using zinc (Zn) in an alkaline medium (e.g., sodium hydroxide);
- by catalytic hydrogenation, using hydrogen in the presence of a catalyst such as Pd/C, Pt/C or Raney-Ni, using hydrazine in the presence of a catalyst such as Pd/C, Pt, Ru and Raney-Ni, or using formic acid (HCOOH) in the presence of Pd/C; or
- by using sulfur compounds, such as, e.g., $H_2S$, NaHS, $Na_2S$, $(NH_4)_2S$, $Na_2S_2O_4$, etc., as reducing agents.

In most cases, when nitro compounds are being reduced to amines in an acidic medium and in cases of catalytic reduction in a neutral medium, the reaction proceeds practically quantitatively and no by-products are formed. However, high cost of the catalysts and the necessity of using hydrogenation equipment are the main disadvantages of these methods.

On the other hand, various by-products, such as azoxy-, azo- or hydrazo-derivatives, are formed in the case of a reduction in an alkaline medium that under these conditions; these by-products do not undergo further reduction to amines. On an industrial scale, this makes it difficult, or even impossible, to isolate a pure amine product. Disadvantages of a reduction using metals in an acidic medium are the formation of considerable amounts of inorganic salts that are wastes hard to dispose of and problems associated with isolating the amine after alkalizing the reaction mixture.

In the next step of Method A, N-(5-amino-2-methylphenyl)-4-(3-pyridinyl)-2-pyrimidineamine is reacted with 4-(4-methylpiperazinemethyl)benzoyl chloride, in the form of a dihydrochloride. The reaction requires a large volume of an organic base, such as pyridine or triethylamine, that binds the evolving hydrogen chloride.

According to Example 21 of EP 0564409 B1, the reaction is carried out by a prolonged heating of reagents in pyridine. No reaction yield is given in the description. One can assume, however, that the yield is not high considering the potential side reactions accompanying the major process. Moreover, the yield is additionally decreased during the removal of pyridine which requires a laborious work-up in order to isolate and purify the final product.

A modification of method A has been proposed in WO 2004/074502, wherein the condensation is carried out in a neutral organic solvent and, although a di(hydrogen halide) of the 4-(4-methylpiperazinemethyl)benzoyl chloride is used as, no hydrogen halide binding agent is used. A tri(hydrogen halide) salt of imatinib, preferably imatinib trihydrochloride in the form of a hydrate, is obtained. The salt precipitates from the solution, thereby facilitating its isolation. The yield of imatinib trihydrochloride hydrate obtained in this step is, however, a mere 53.5%; and another conversion step to liberate the imatinib free base is required, further decreasing the total yield. The yield of converting trihydrochloride into imatinib base is not revealed in the description but the combined yield of two steps cannot be considered as high.

In Method B, (3-pyridinyl)-2-pyrimideineamine, or a precursor thereof, is reacted with 4-methylphenyl-(4-methylpiperazin-1-ylmethyl)benzamide.

In one variation of Method B (Example 9 of WO 03/066613), a suspension of N-(3-guanidine-4-methylphenyl)-4-(4-methylpiperazin-1-ylmethyl)-benzamide is heated in n-butanol with a slight molar excess of 3-dimethylamino-1-pyridin-3-ylpropenone. The process requires high temperature and has to be carried out under an inert gas atmosphere. The product is isolated by distilling off dimethylamine and n-butanol, making up its amount in the reaction mixture during distillation, and then precipitating the product using butyl acetate.

Another variation of Method B (Example 10 of WO 03/066613) comprises the reaction of N-(3-bromo-4-methylphenyl)-4-(4-methylpiperazin-1-ylmethyl)benzamide with 4-(3-pyridinyl)-2-pyrimidineamine in the presence of sodium tert-butoxide and a catalytic amount of $Pd_2(dba)_3$-rac-BINAP. Despite a relatively high yield of the last step of condensing the key synthons of the compound, the synthesis of imatinib by this method is difficult to scale up as it requires expensive catalysts, special sonication equipment, as well as tedious purification of the product by flash chromatography on silica gel, and separating the desired from the undesired isomers using reverse-phase preparative chromatography.

The variation of Method C described in J. Med. Chem. 2005, 48(1), 249-255 is not of significant practical importance. It uses expensive analytical-grade reagents and the yields obtained in subsequent steps are rather poor. Namely, the yield of the reaction of 4-methyl-N-3-((4-pyridin-3-yl)pyrimidin-2-yl)benzene-1,3-diamine with 4-chloromethylbenzoyl chloride in dimethylformamide is 61% after recrystallization of the product from ethyl acetate, and the yield of the reaction of 4-chloromethyl-N-(4-methyl-3-(4-(pyridin-3-yl)pyrimidin-2-ylamino)phenyl)benzamide with N-methylpiperazine is 68%, after recrystallizing the product from acetonitrile.

In sum, novel solutions that would speed up and improve the total synthesis of imatinib base are needed. Specifically, it is of particular importance to develop methods that would allow for increased yields of individual steps with the goal of improving the yield of the overall transformation and economic efficiency, with an eye on industrial scalability.

BRIEF SUMMARY OF THE INVENTION

The invention provides a process for preparation of imatinib base and pharmaceutically acceptable acid addition salts thereof, comprising (a) reacting 2-methyl-5-nitroaniline with cyanamide in the presence of hydrochloric acid to obtain 1-(2-methyl-5-nitrophenyl)guanidine hydrochloride; (b) converting 1-(2-methyl-5-nitrophenyl)guanidine hydrochloride to 1-(2-methyl-5-nitrophenyl)guanidine nitrate; (c) condensing 3-acetylpyridine with N,N-dimethylformamide dimethyl acetal to obtain 3-(dimethylamino)-1-(3-pyridinyl)-prop-2-en-1-one; (d) reacting 3-(dimethylamino)-1-(3-pyridinyl)-prop-2-en-1-one with 1-(2-methyl-5-nitrophenyl)guanidine nitrate to obtain N-(5-nitro-2-methylphenyl)-4-(3-pyridinyl)-2-pyrimidineamine; (e) reducing N-(5-nitro-2-methylphenyl)-4-(3-pyridinyl)-2-pyrimidineamine using hydrazine in the presence of Raney nickel to obtain N-(5-amino-2-methylphenyl)-4-(3-pyridinyl)-2-pyrimidineamine; (f) condensing N-(5-amino-2-methylphenyl)-4-(3-pyridinyl)-2-pyrimidine-amine with 4-chloromethylbenzoyl chloride in the presence of an inorganic base to obtain 4-chloromethyl-N-(4-methyl-3-(4-(pyridin-3-yl)pyrimidin-2-ylamino)phenyl)benzamide; (g) condensing 4-chloromethyl-N-(4-methyl-3-(4-(pyridin-3-yl)pyrimidin-2-ylamino)phenyl)benzamide with an excess of N-methylpiperazine to obtain imatinib base; adding water or a mixture of water and an organic solvent; and isolating said imatinib base; and (h) optionally, converting imatinib base to a pharmaceutically acceptable acid addition salt of imatinib base.

In certain embodiments of the invention, methanol is being removed in a continuous or periodical manner, and particularly in a periodical manner, while condensing said 3-acetylpyridine with said N,N-dimethylformamide dimethyl acetal.

In certain embodiments of the invention, condensing 3-acetylpyridine with N,N-dimethylformamide dimethyl acetal is carried out using between about 1.2 and about 2.0 molar equivalents, and particularly about 1.5 molar equivalents, of N,N-dimethylformamide dimethyl acetal with respect to 3-acetylpyridine.

In certain embodiments of the invention, reducing N-(5-nitro-2-methylphenyl)-4-(3-pyridinyl)-2-pyrimidineamine using hydrazine in the presence of Raney nickel is carried out using an excess of hydrazine with respect to N-(5-nitro-2-methylphenyl)-4-(3-pyridinyl)-2-pyrimidineamine, and particularly using between about 2 and about 8 molar equivalents of hydrazine with respect to N-(5-nitro-2-methylphenyl)-4-(3-pyridinyl)-2-pyrimidineamine.

In certain embodiments of the invention, hydrazine is provided in the form of hydrazine hydrate or an aqueous solution of hydrazine hydrate.

In certain embodiments of the invention, Raney nickel is used in an amount of not less than approximately 10% by weight with respect to N-(5-nitro-2-methylphenyl)-4-(3-pyridinyl)-2-pyrimidineamine.

In certain embodiments of the invention, reducing N-(5-nitro-2-methylphenyl)-4-(3-pyridinyl)-2-pyrimidineamine using hydrazine in the presence of Raney nickel is carried out in a $C_1$-$C_4$ alcohol, a $C_1$-$C_4$ aliphatic ether, or a cyclic ether, as solvent, and particularly is carried out in methanol.

In certain embodiments of the invention, reducing N-(5-nitro-2-methylphenyl)-4-(3-pyridinyl)-2-pyrimidineamine using hydrazine in the presence of Raney nickel to obtain N-(5-amino-2-methylphenyl)-4-(3-pyridinyl)-2-pyrimidineamine does not also result in the formation of compounds represented by formula 1a and formula 1b:

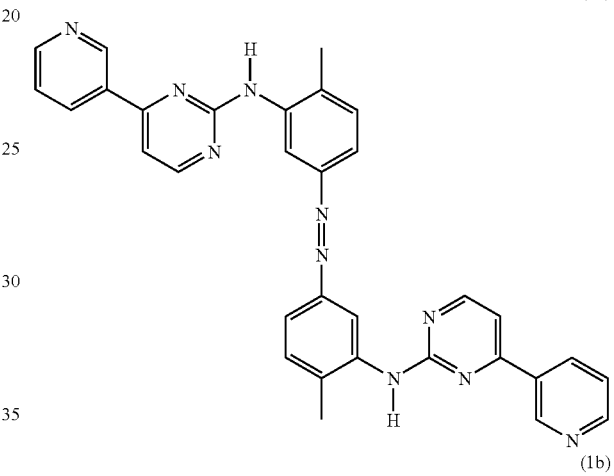

(1a)

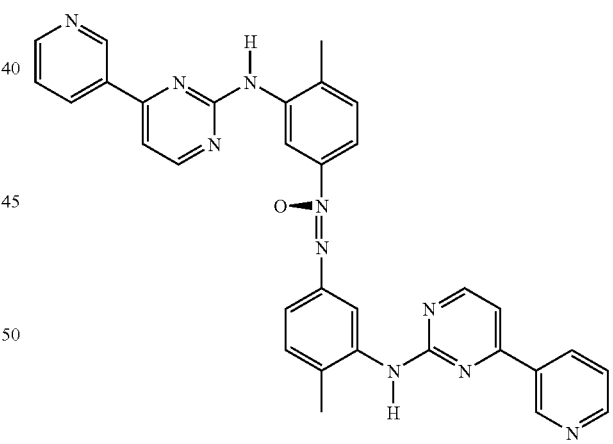

(1b)

In certain embodiments of the invention, the inorganic base is potassium carbonate.

In certain embodiments of the invention, after condensing N-(5-amino-2-methylphenyl)-4-(3-pyridinyl)-2-pyrimidineamine with 4-chloromethylbenzoyl chloride in the presence of an inorganic base to obtain 4-chloromethyl-N-(4-methyl-3-(4-(pyridin-3-yl)pyrimidin-2-ylamino)phenyl)benzamide, water is added, and 4-chloromethyl-N-(4-methyl-3-(4-(pyridin-3-yl)pyrimidin-2-ylamino)phenyl)benzamide is isolated by filtration.

In certain embodiments of the invention, condensing 4-chloromethyl-N-(4-methyl-3-(4-(pyridin-3-yl)pyrimidin-2-ylamino)phenyl)benzamide with an excess of N-methylpiperazine is carried out using between about 2 and about 12 molar equivalents of N-methylpiperazine with respect to 4-chloromethyl-N-(4-methyl-3-(4-(pyridin-3-yl)pyrimidin-2-ylamino)phenyl)benzamide, and particularly is carried out using between about 5 and about 7 molar equivalents of N-methylpiperazine with respect to 4-chloromethyl-N-(4-methyl-3-(4-(pyridin-3-yl)pyrimidin-2-ylamino)phenyl) benzamide.

In certain embodiments of the invention, after condensing 4-chloromethyl-N-(4-methyl-3-(4-(pyridin-3-yl)pyrimidin-2-ylamino)phenyl)benzamide with an excess of N-methylpiperazine to obtain imatinib base, and adding water or a mixture of water and an organic solvent; the reaction mixture is neutralized.

In certain embodiments of the invention, the organic solvent is selected from the group of $C_1$-$C_4$ aliphatic alcohols and $C_1$-$C_4$ ketones.

In certain embodiments of the invention, imatinib base is isolated by filtration.

In other aspects the invention provides a process for the preparation of N-(5-nitro-2-methylphenyl)-4-(3-pyridinyl)-2-pyrimidineamine comprising: (a) reacting 2-methyl-5-nitroaniline with cyanamide in the presence of hydrochloric acid to obtain 1-(2-methyl-5-nitrophenyl)guanidine hydrochloride; (b) converting 1-(2-methyl-5-nitrophenyl)guanidine hydrochloride to 1-(2-methyl-5-nitrophenyl)guanidine nitrate; (c) condensing 3-acetylpyridine with N,N-dimethylformamide dimethyl acetal to obtain 3-(dimethylamino)-1-(3-pyridinyl)-prop-2-en-1-one; and (d) reacting 3-(dimethylamino)-1-(3-pyridinyl)-prop-2-en-1-one with 1-(2-methyl-5-nitrophenyl)guanidine nitrate to obtain N-(5-nitro-2-methylphenyl)-4-(3-pyridinyl)-2-pyrimidineamine.

In other aspects the invention provides a process for the preparation of N-(5-amino-2-methylphenyl)-4-(3-pyridinyl)-2-pyrimidine-amine comprising reducing N-(5-nitro-2-methylphenyl)-4-(3-pyridinyl)-2-pyrimidineamine using hydrazine in the presence of Raney nickel to obtain N-(5-amino-2-methylphenyl)-4-(3-pyridinyl)-2-pyrimidine-amine.

In other aspects the invention provides a process for the preparation of 4-chloromethyl-N-(4-methyl-3-(4-(pyridin-3-yl)pyrimidin-2-ylamino)phenyl)benzamide comprising condensing N-(5-amino-2-methylphenyl)-4-(3-pyridinyl)-2-pyrimidine-amine with 4-chloromethylbenzoyl chloride in a free form in the presence of an inorganic base to obtain 4-chloromethyl-N-(4-methyl-3-(4-(pyridin-3-yl)pyrimidin-2-ylamino)phenyl)benzamide.

In other aspects the invention provides a process for the preparation of imatinib base comprising condensing 4-chloromethyl-N-(4-methyl-3-(4-(pyridin-3-yl)pyrimidin-2-ylamino)phenyl)benzamide with an excess of N-methylpiperazine to obtain imatinib base.

BRIEF DESCRIPTION OF THE SEVERAL VIEWS OF THE DRAWING(S)

Not Applicable

DETAILED DESCRIPTION OF THE INVENTION

The invention provides an improved process for the preparation of imatinib base that ensures high yields of the individual steps in the synthesis, and technologically simple methods for isolating and purifying the intermediates thereof. The synthetic pathway is outlined in Scheme 4 below.

Successive steps of the process according to the invention are carried out in the following way.

I. N-(5-Nitro-2-methylphenyl)-4-(3-pyridinyl)-2-pyrimidineamine

N-(5-Nitro-2-methylphenyl)-4-(3-pyridinyl)-2-pyrimidineamine is obtained by condensing 3-acetylpyridine with N,N-dimethylformamide dimethyl acetal under conditions favorable for the removal methanol formed in the reaction.

The condensation of 3-acetylpyridine with N,N-dimethylformamide dimethyl acetal is carried out using a slight molar excess, particularly 1.2-2.0 equivalents of the acetal per 1 equivalent of 3-acetylpyridine, and more particularly 1.5 equivalents of the acetal per 1 equivalent of 3-acetylpyridine.

N,N-Dimethylformamide dimethyl acetal provides a suitable medium for the reaction. Alternatively, the reaction is carried out in a neutral organic solvent, the boiling temperature of which is not lower than that of the acetal used in the reaction.

The condensation is carried out at a temperature corresponding to the boiling point of the reaction mixture until 3-acetylpyridine is no longer visible by TLC. The reaction time in the case of using N,N-dimethylformamide dimethyl acetal is generally shorter when compared to the reaction time in other media disclosed elsewhere.

Scheme 4

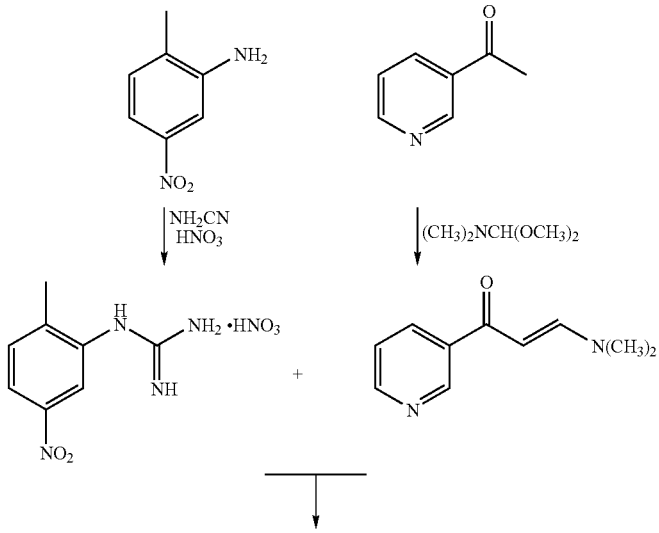

-continued

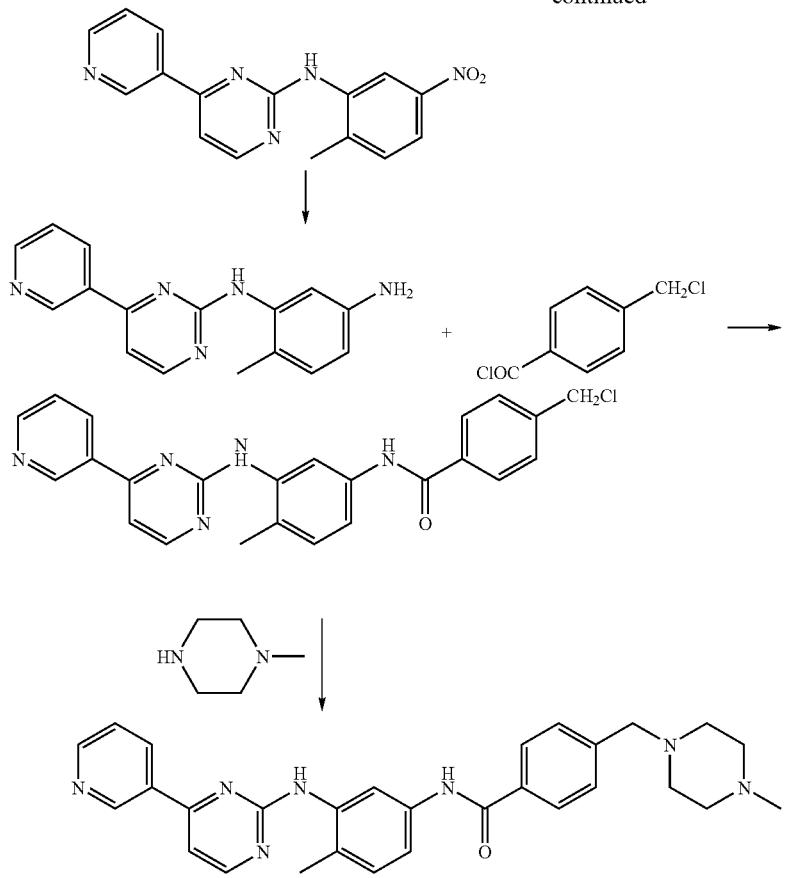

Methanol formed in the reaction is removed from the reaction mixture by any method known in the art, e.g., by distillation, in a continuous way or periodically (i.e., in certain time intervals during the reaction, or on a one-time basis after the completion of the reaction) using a distillation apparatus provided with a Vigreux column.

A crude reaction product is obtained by distilling off the excess acetal and the additional organic solvent, if any. The product is used without further purification in the next step of the synthesis after dissolving it in a suitable neutral solvent, preferably N,N-dimethylformamide, and adding a guanidine nitrate derivative and a base, if deemed necessary.

Bases used in this step are selected from salts of alkaline metals and alkaline earth metals, such as carbonates and bicarbonates, and hydroxides of alkaline metals, such as sodium and potassium hydroxides.

After completion of the reaction, the crude product is isolated by standard methods well-known in the art, e.g. by filtration, and is then dried and further purified, if deemed necessary. In general, the product obtained by the process does not require additional purification and can be used crude in the next step of the synthesis.

Crude 3-(dimethylamino)-1-(3-pyridinyl)-prop-2-en-1-one is reacted with 1-(2-methyl-5-nitrophenyl)guanidine nitrate without any purification.

The starting material, 1-(2-methyl-5-nitrophenyl)guanidine nitrate is obtained independently in a more efficient way as compared to prior art processes, i.e., by reacting 2-methyl-5-nitroaniline with cyanamide in the presence of concentrated hydrochloric acid, and then converting the guanidine hydrochloride derivative into a nitrate by treating it with concentrated nitric acid.

The yield of N-(5-nitro-2-methylphenyl)-4-(3-pyridinyl)-2-pyrimidineamine is over 73%, calculated based on 3-acetylpyridine.

II. N-(5-Amino-2-methylphenyl)-4-(3-pyridinyl)-2-pyrimidine-amine

N-(5-nitro-2-methylphenyl)-4-(3-pyridinyl)-2-pyrimidineamine is reduced to N-(5-amino-2-methylphenyl)-4-(3-pyridinyl)-2-pyrimidineamine using hydrazine in the presence of Raney's nickel.

It has been found that certain conditions of carrying out the process reduce to minimum the amounts of by-products formed in the reaction and facilitate the isolation and purification of the product.

In certain circumstances, as for example, an insufficient activity of Raney's nickel (e.g., in the case of using recovered Raney's nickel), a too low amount of the catalyst, a too low the addition rate of hydrazine, or if the crude nitro compound is wet, undesired reduction by-products are formed in the reaction. Removal of the by-products during purification of crude N-(5-amino-2-methylphenyl)-4-(3-pyridinyl)-2-pyrimidineamine is difficult, as these compounds are crystallizing much more readily than the desired product of the reaction. Moreover, it was found that when hydrazine is used in the presence of Raney's nickel as a catalyst, these by-products are not reduced to amines, which makes their removal impossible for practical purposes.

The structure of the major by-products has been determined by proton magnetic resonance, $^1$H-NMR, and by combustion analysis to include structure 1a corresponding to the azo-derivative, and structure 1b corresponding to the azoxy-derivative, as represented by formulas below.

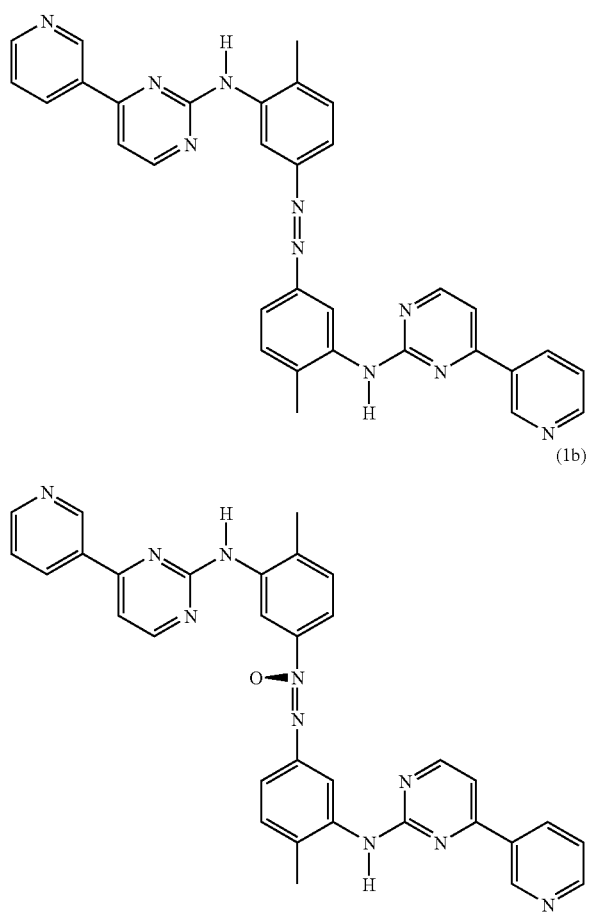

In a preferred embodiment of the invention, the reduction of N-(5-nitro-2-methylphenyl)-4-(3-pyridinyl)-2-pyrimidineamine to N-(5-amino-2-methylphenyl)-4-(3-pyridinyl)-2-pyrimidineamine is accomplished by using commercially available hydrazine hydrate, or aqueous solutions thereof, e.g., a 40% or 80% solution (wt.).

One factor that is crucial for decreasing the level of by-products is carrying out the process while maintaining an excess of hydrazine in the reaction medium. Usually, about 2 to 8 moles, and preferably about 3 to 4.5 moles of hydrazine hydrate are used per 1 mole of N-(5-nitro-2-methylphenyl)-4-(3-pyridinyl)-2-pyrimidineamine. Hydrazine hydrate is added to the reaction mixture in one portion, or in two or more portions.

In order to ensure a proper course of the reaction not less than approximately 10% by weight of Raney's nickel accounting based on the dry N-(5-nitro-2-methylphenyl)-4-(3-pyridinyl)-2-pyrimidineamine is used. Favorable reduction conditions are achieved by using Raney's nickel of a high activity.

The reaction is carried out in an aliphatic alcohol, such as methanol, isopropanol, 2-methoxyethanol or in an aliphatic or cyclic ether such as tetrahydrofuran, dioxane or 1,2-dimethoxyethane. Preferably, the reduction is carried out in methanol.

The process is carried out by adding hydrazine hydrate to a suspension of the nitro compound dropwise at a temperature ranging from room temperature to the boiling point of the reaction mixture, until the starting material is no longer detectable by TLC, and then isolating the product by a standard work-up.

Using hydrazine in the reduction allows the product to be easily isolated and purified. The yield of the product exceeds 80% and its purity is greater than 99.5% (by HPLC). The use of inexpensive and readily available reagents allows the process to be scaled up to a full industrial scale.

III. 4-Chloromethyl-N-(4-methyl-3-(4-(pyridin-3-yl) pyrimidin-2-ylamino)phenyl)benzamide 6-Methyl-N'-(4-(pyridin-3-yl)pyrimidin-2-yl)benzene-1,3-diamine is reacted with 4-chloromethylbenzoyl chloride in the presence of a base to obtain 4-chloromethyl-N-(4-methyl-3-(4-(pyridin-3-yl)pyrimidin-2-ylamino)phenyl)benzamide.

Unlike other solutions for the synthesis of 4-chloromethyl-N-(4-methyl-3-(4-(pyridin-3-yl)pyrimidin-2-ylamino)phenyl)benzamide which generally employ the 4-(4-methylpiperazinemethyl)benzoyl chloride, this process uses the readily available 4-chloromethylbenzoyl chloride in its free form (i.e., not the hydrochloride form).

The reaction is carried out in a neutral organic solvent such as tetrahydrofuran, dioxane or dimethylsulfoxide.

A base is used in an amount sufficient for binding the theoretical amount of hydrogen chloride present in the reaction medium. Any organic base is suitable, such as a tertiary amine, e.g., triethylamine, or inorganic base, such as a carbonate or bicarbonate salt of alkaline metals, e.g., potassium carbonate, sodium carbonate or sodium bicarbonate. Potassium carbonate is particularly preferred. In the work-up, the reaction mixture is diluted with water and the precipitated product is isolated by filtration.

Usually, the yield of this step of the synthesis exceeds 95%.

IV. N-(4-methyl-3-(4-(pyridin-3-yl)pyrimidin-2-ylamino)phenyl)-4-((4-methylpiperazin-1-yl)methyl) benzamide 4-chloromethyl-N-(4-methyl-3-(4-(pyridin-3-yl)pyrimidin-2-ylamino)phenyl)benzamide obtained in the previous step is reacted with N-methylpiperazine. The reaction is carried out using a molar excess of N-methylpiperazine which doubles as solvent. Alternatively, the reaction is carried out in a neutral organic solvent, e.g., a cyclic ether.

The molar excess of N-methylpiperazine is from about 2 to about 12, and preferably from about 5 to about 7 equivalents with respect to 4-chloromethyl-N-(4-methyl-3-(4-(pyridin-3-yl)pyrimidin-2-ylamino)phenyl)benzamide. In general, the reaction is carried out at temperature 120-140° C. for 1.5-3 hours.

After completion of the reaction, water or a mixture of water and an organic solvent, selected from lower aliphatic alcohols or ketones, is added to the reaction mixture, and the reaction medium is neutralized, if necessary, with an aqueous solution of an alkaline metal hydroxide or a bicarbonate. A formed precipitate is isolated, e.g., by filtration, and dried in air to afford a crystalline product of high chromatographic purity with the yield of over 90%. Conventional purification technique, e.g., single recrystallization, is sufficient for obtaining a product complying with pharmacopoeial purity requirements.

The steps of the process according to the invention provide an improved and efficient process for preparation of imatinib base. The process employs simple starting materials and reagents, while simultaneously avoiding laborious isolation and purification of intermediates and the final product, thereby facilitating a further improvements and scale-up.

The total yield of imatinib base obtained by the process according to the invention is over 45%, compared to approximately 15% reported for prior art processes.

This invention is not to be limited to the specific embodiments disclosed hereiri and modifications for various applications and other embodiments are intended to be included within the scope of the appended claims. While this invention has been described in connection with particular examples thereof, the true scope of the invention should not be so limited since other modifications will become apparent to the skilled practitioner upon a study of the drawings, specification, and following claims.

All publications and patent applications mentioned in this specification are indicative of the level of skill of those skilled in the art to which this invention pertains. All publications and patent applications mentioned in this specification are herein incorporated by reference to the same extent as if each individual publication or patent application mentioned in this specification was specifically and individually indicated to be incorporated by reference.

The following examples are provided to illustrate the invention. The examples are not meant to limit the scope of the invention as defined in the claims.

EXAMPLES 1-(2-Methyl-5-nitrophenyl)guanidine nitrate

Example 1

20 g of 2-Methyl-5-nitroaniline (0.131 mol; 1 eq.), 11.05 g of cyanamide (0.263 mol; 2 eq.) and 80 mL of isopropyl alcohol were placed in a reactor flask. The reaction mixture was heated to 80° C., and 18 mL of concentrated hydrochloric acid was slowly added dropwise within 80 minutes. The reaction mixture was stirred for 1 hour while maintaining the temperature at 80° C. Next, 6 mL of concentrated hydrochloric acid was added dropwise and the reaction mixture was kept at 80° C. for 2 hours. The reaction mixture was cooled down to 60° C. and 10 mL of 65% nitric acid (0.142 mol, 1.08 eq.) was added dropwise and the mixture was left with stirring until it was cooled down to room temperature. The solid product was filtered off, washed with 50 mL of isopropyl alcohol and dried in the air to afford 27.45 g (yield 81.1%) of 1-(2-methyl-5-nitrophenyl)guanidine nitrate, m.p. 203-206° C.; $^1$H NMR (DMSO-$d_6$, 200 MHz): 2.32 (3H, s, $CH_3$), 7.44 (4H, m, 4×NH), 7.64 (1H, d, J=8.2 Hz, 3-H), 8.09 (1H, d, J=2.5 Hz, 6-H), 8.15 (1H, dd, J=8.2 i 2.5 Hz, 4-H), 9.51 (1H, m, $NH^+$).

N-(5-Nitro-2-methylphenyl)-4-(3-pyridinyl)-2-pyrimidineamine

Example 2

26.60 g of 3-acetylpyridine (0.219 mol; 1 eq.) and 44.0 mL of N,N-dimethylformamide dimethyl acetal (39.47 g; 0.331 mol; 1.508 eq.) were placed in a reactor flask and the mixture was refluxed for 1.5 h. Methanol, produced in the reaction was removed by distillation and the mixture was refluxed for further 2 hours. The rest of methanol and excess of the acetal were removed by distillation under slightly reduced pressure. The hot residue was treated with 100 mL DMF, and, after cooling down, with 56.3 g of 1-(2-methyl-5-nitrophenyl) guanidine nitrate (0.219 mol; 1 eq.). A solution of 8.8 g of sodium hydroxide in 17 mL of water was then added dropwise and the mixture was refluxed for 8 hours in an oil bath. Water (200 mL) was added with care to the hot solution, and the contents of the flask were poured to 700 mL of warm water. The whole mixture was cooled with stirring to room temperature. The precipitated solid was isolated by filtration and dried in the air to afford 49.41 g of crude 2-(2-methyl-5-nitroanilino)-4-(3-pyridinyl)pyrimidine (yield 73.2% calculated on 3-acetylpyridine), m.p. 186-188° C.; $^1$H NMR (DMSO-$d_6$, 200 MHz): 2.43 (3H, s, $CH_3$), 7.54 (3H, m, 3-H phenyl +5-H pyrimidine +5-H pyridyl), 7.90 (1H, dd, J=8.2, 2.2 Hz, 4-H phenyl), 8.48 (1H, dt, $J_1$=7.9 Hz, 4-H pyridyl), 8.62 (1H, d, J=5.4 Hz, 6-H pyrimidine), 8.71 (1H, dd, 6-H pyridyl), 8.79 (1H, d, J=2.2 Hz, 6-H phenyl), 9.27 (1H, s, NH), 9.32 (1H, d, J=1.6 Hz, 2-H pyridyl).

N-(5-Amino-2-methylphenyl)-4-(3-pyridinyl)-2-pyrimidineamine

Example 3

To a stirring suspension of N-(5-nitro-2-methylphenyl)-4-(3-pyridinyl)-2-pyrimidineamine (65 g; 0.21 mol) in methanol (1400 mL) was added wet Raney's nickel (6.25 g) followed by the first portion of an 80% solution of hydrazine hydrate (52.5 g; 0.84 mol) in methanol (50 mL). After 1 hour, the reaction mixture was cooled down to 35° C. and stirring was continued for further 1.5 hour. Next, the second portion of an 80% solution of hydrazine hydrate (52.5 g; 0.84 mol) in methanol (50 mL) was added dropwise and stirring was continued for 3 hours. The reaction mixture was cooled down to room temperature and filtered through a pad of Celite. The layer of Celite was washed with methanol (150 mL). The combined filtrates were concentrated in vacuo, treated with dichloromethane (500 mL), and the organic layer was washed with water (3×300 mL). The organic layer was dried with anhydrous $MgSO_4$ (12 g) and filtered through a pad of $SiO_2$ (60 g). The layer of silica gel was washed subsequently with a mixture of dichloromethane-ethyl acetate (50:50; 300 mL) and ethyl acetate (600 mL). The combined filtrates were concentrated under normal pressure to approximately 100 mL and cooled down with stirring to room temperature. The crystalline solid was filtered off and washed with a small volume of dichloromethane to afford 47.5 g (80.9%) of the title product. Purity (by HPLC): 99.84%.

Example 4

Wet Raney Nickel (2.5 g) was added to a stirring suspension of N-(5-nitro-2-methylphenyl)-4-(3-pyridinyl)-2-pyrimidineamine (24 g; 78.1 mmol) in methanol (380 mL). The mixture was heated to reflux and the first portion of a 40% solution of hydrazine hydrate (10 mL; 79.9 mmol) was added dropwise. After refluxing the mixture for 20 minutes, the second portion of a 40% solution of hydrazine hydrate (10 mL; 79.9 mmol) was added dropwise. After 40 minutes of refluxing, the reaction mixture was cooled down to room temperature and filtered through a pad of Celite. The Celite was washed with methanol (150 mL). The combined filtrates were concentrated in vacuo. The residue was treated with dichloromethane (300 mL) and active charcoal (2.5 g) and then refluxed for 30 minutes. After cooling the reaction mixture to room temperature, charcoal was filtered off and washed with dichloromethane (100 mL). Next, the procedure described in Example 3 was followed to afford 16.552 g (76.4%) of the title product. Purity (by HPLC): 99.64%.

Example 5

Wet Raney's nickel (2.5 g) was added to a stirring suspension of N-(5-nitro-2-methylphenyl)-4-(3-pyridinyl)-2-pyrimidineamine (24 g; 78.1 mmol) in methanol (380 mL). The mixture was heated to reflux and the first portion of an 80% solution of hydrazine hydrate (7.5 mL; 119.9 mmol) was added dropwise. After refluxing the mixture for 20 minutes, the second portion of an 80% solution of hydrazine hydrate (7.5 mL; 119.9 mmol) was added dropwise. After 40 minutes of refluxing, the reaction mixture was cooled down to room temperature and filtered through a pad of Celite. The layer of Celite was washed with methanol (100 mL). The combined filtrates were concentrated in vacuo. The residue was treated with dichloromethane (200 mL) and active charcoal (2.5 g) and then refluxed for 30 minutes. After cooling the reaction mixture to room temperature, charcoal was filtered off and washed with dichloromethane (100 mL). Next, the procedure described in Example 3 was followed to afford 15.886 g (73.2%) of the product. Purity (by HPLC): 99.75%.

4-Chloromethyl-N-(4-methyl-3-(4-(pyridin-3-yl) pyrimidin-2-ylamino)phenyl)benzamide Example 6

6-methyl-N'-(4-(pyridin-3-yl)pyrimidin-2-yl)benzene-1, 3-diamine (18.488 g, 0.067 mol) was dissolved in THF (255 mL), freshly ground potassium carbonate (19.870 g, 0.143 mol) was added and then the mixture was cooled down to 0° C. A solution of 4-chloromethylbenzoyl chloride (13.863 g, 0.073 mol) in THF (69 mL) was added dropwise within 15 minutes while temperature of the reaction mixture was maintained at 0° C. The reaction mixture was stirred at this temperature for 2 hours and for another 2 hours at room temperature. Water was added dropwise at a very slow rate. The temperature of the reaction rose to 26° C. At this temperature dropwise addition of water was continued with cooling. Cooling was discontinued when temperature dropped below 19° C. When water addition was completed (in total 543 mL), temperature of the reaction mixture was 26° C. The reaction mixture was stirred for further 30 min. A solid precipitate was filtered off and washed with water (150 mL) to afford 28.06 g (yield 97%) of the title compound in the form of a colorless crystalline solid; m.p. 211-212° C.; $^1$H NMR (DMSO-d$_6$): 10.24 (1H, s), 9.28 (1H, d, J=1.8), 8.99 (1H, s), 8.69 (1H, dd, J=4.8-1.4), 8.52 (1H, d, J=5.2), 8.48 (1H, dt, J=8.2-1.8), 8.09 (1H, d, J=2.0), 7.96 (2H, d, J=8.0), 7.51 (5H, m), 7.22 (1H, d, J=8.4), 4.85 (2H, s), 2.23 (31H, s).

Example 7

6-methyl-N$^1$-(4-(pyridin-3-yl)pyrimidin-2-yl)benzene-1, 3-diamine (18.488 g, 0.067 mol) was dissolved in THF (255 mL), freshly ground potassium carbonate (19.870 g, 0.143 mol) was added and then the mixture was cooled down to 0° C. A solution of 4-chloromethylbenzoyl chloride (13.863 g, 0.073 mol) in THF (69 mL) was added dropwise within 10 minutes while temperature of the reaction mixture was maintained at approximately 20° C. The reaction mixture was stirred at room temperature for 1 hour. Water was added dropwise (543 mL in total) while maintaining temperature of the reaction mixture at approximately 20° C., and then the reaction mixture was stirred for 80 min. A solid precipitate was filtered off and washed with water (150 mL) to afford 28.37 g (yield 98%) of the title compound.

Example 8

6-methyl-N$^1$-(4-(pyridin-3-yl)pyrimidin-2-yl)benzene-1, 3-diamine (9.244 g, 33.3 mmol) was dissolved in THF (128 mL), then a solution of potassium carbonate (9.935 g, 71.9 mmol) in water (13 mL) was poured in. The mixture was cooled down to 0° C. and a solution of 4-chloromethylbenzoyl chloride (6.932 g, 36.7 mmol) in THF (30 mL) was added dropwise within 15 minutes. The reaction mixture was stirred at 0° C. for 2 hours. Water (260 mL) was added dropwise with stirring and cooling the reaction flask and then at room temperature for further 30 min. A solid precipitate was filtered off and washed with water (120 mL) to afford 13.62 g (yield 95%) of the title compound.

N-(4-methyl-3-(4-(pyridin-3-yl)pyrimidin-2-ylamino)phenyl)-4-((4-methylpiperazin-1-yl)methyl) benzamide Example 9

A flask containing a mixture of 4-chloromethyl-N-(4-methyl-3-(4-(pyridin-3-yl)pyrimidin-2-ylamino)phenyl)benzamide obtained in the previous step (56.072 g; 0.130 mol), N-methylpiperazine (84 mL; 75.852 g; 0.757 mol) and dioxane (56 mL) was placed in an oil bath at temperature 135° C. and the reaction mixture was heated for 3 hours. After that time the oil bath was taken away and after cooling the reaction mixture, acetone (150 mL) was added and stirring was continued until the mixture was cooled down to room temperature. The precipitated product was filtered off, washed with cold acetone (50 mL) and dried in the air to afford 59.2 g (yield 91%) of the title compound in the form of a cream-coloured, crystalline solid; m.p. 167-170° C.; $^1$H NMR (DMSO-d$_6$): 10.16 (1H, s), 9.27 (1H, d, J=2.2), 8.98 (1H, s), 8.68 (1H, dd, J=4.8-1.6), 8.51 (1H, d, J=5.3), 8.48 (1H, dt, J=8.2-2.0), 8.08 (1H, d, J=1.8), 7.90 (2H, d, J=8.2), 7.45 (5H, m), 7.20 (1H, d, J=8.6), 3.52 (2H, s), 2.35 (8H, m), 2.22 (3H, s), 2.15 (3H, s).

Example 10

A flask containing a mixture of 4-chloromethyl-N-(4-methyl-3-(4-(pyridin-3-yl)pyrimidin-2-ylamino)phenyl)benzamide (55.276 g; 0.129 mol) and N-methylpiperazine (83 mL; 74.949 g; 0.748 mol) was placed in an oil bath at a temperature of 120-125° C. and the reaction mixture was heated for 90 minutes. After that time the oil bath was taken away, isopropanol (300 mL) was added to the hot mixture, and the stirring was continued until the mixture was cooled down to room temperature. A precipitate was filtered off, washed with cold isopropanol (50 mL) and dried in the air to afford 58.7 g (92%) of the title product.

Example 11

A flask containing a mixture of 4-chloromethyl-N-(4-methyl-3-(4-(pyridin-3-yl)pyrimidin-2-ylamino)phenyl)benzamide (54.953 g; 0.129 mol) and N-methylpiperazine (83 mL; 74.949 g; 0.748 mol) was placed in an oil bath at a temperature of 120-125° C. and the reaction mixture was heated for 90 minutes. After that time the oil bath was taken away, isopropanol (200 mL) was added to the hot mixture and the stirring was continued until the mixture was cooled down to room temperature. The precipitated product was filtered off, washed with a mixture of isopropanol and water (1:1, 100 mL) and dried in the air to afford 57.7 g (91%) of the product.

Example 12

A flask containing a mixture of 4-chloromethyl-N-(4-methyl-3-(4-(pyridin-3-yl)pyrimidin-2-ylamino)phenyl)benzamide (54.949 g; 0.129 mol) and N-methylpiperazine (83 mL; 74.949 g; 0.748 mol) was placed in an oil bath at temperature 120-125° C. and the reaction mixture was heated for 90 minutes. After that time the oil bath was taken away, water (100 mL) was added to the hot mixture and stirring was continued until the mixture was cooled down to room temperature. A precipitate was filtered off and the residue was removed from the flask with water (80 mL). The combined precipitate was washed with water (3×100 mL) to afford 60.2 g (95%) of the product.

Example 13

A flask containing a mixture of 4-chloromethyl-N-(4-methyl-3-(4-(pyridin-3-yl)pyrimidin-2-ylamino)phenyl)benzamide (55.000 g; 0.128 mol) and N-methylpiperazine (83 mL; 74.949 g; 0.748 mol) was placed in a cold oil bath and the reaction mixture was heated until the bath temperature has reached 130° C. Heating at that temperature was continued for 90 minutes. After that time the oil bath was taken away, and when the temperature of the reaction mixture dropped to 95° C., water (100 mL) was added. Stirring was continued until the mixture was cooled down to room temperature. A solution of sodium hydroxide (5.12 g) in water (100 mL) was added and the mixture was stirred for 30 min. The precipitated product was filtered off and washed with water (300 mL) to afford 60.6 g (96%) of the title product.

SEQUENCE LISTING

Not applicable

The invention claimed is:
1. A process for the preparation of imatinib base and pharmaceutically acceptable acid addition salts thereof, comprising:
 (a) reacting 2-methyl-5-nitroaniline with cyanamide in the presence of hydrochloric acid to obtain 1-(2-methyl-5-nitrophenyl)guanidine hydrochloride;
 (b) converting 1-(2-methyl-5-nitrophenyl)guanidine hydrochloride to 1-(2-methyl-5-nitrophenyl)guanidine nitrate;
 (c) condensing 3-acetylpyridine with N,N-dimethylformamide dimethyl acetal to obtain 3-(dimethylamino)-1-(3-pyridinyl)-prop-2-en-1-one; and in situ, without isolation and purification, reacting said 3-(dimethylamino)-1-(3-pyridinyl)-prop-2-en-1-one with 1-(2-methyl-5-nitrophenyl)guanidine nitrate to obtain N-(5-nitro-2-methylphenyl)-4-(3-pyridinyl)-2-pyrimidineamine;
 (d) reducing N-(5-nitro-2-methylphenyl)-4-(3-pyridinyl)-2-pyrimidineamine using a permanent excess of hydrazine in the presence of Raney nickel to obtain N-(5-amino-2-methylphenyl)-4-(3-pyridinyl)-2-pyrimidineamine;
 (e) condensing N-(5-amino-2-methylphenyl)-4-(3-pyridinyl)-2-pyrimidine-amine with 4-chloromethylbenzoyl chloride in the presence of an inorganic base to obtain 4-(chloromethyl)-N-(4-methyl-3-(4-(pyridin-3-yl)pyrimidin-2-ylamino)phenyl)benzamide;
 (f) condensing 4-(chloromethyl)-N-(4-methyl-3-(4-(pyridin-3-yl)pyrimidin-2-ylamino)phenyl)benzamide with an excess of N-methylpiperazine to obtain imatinib base; adding water or a mixture of water and an organic solvent; and isolating said imatinib base; and
 (g) optionally, converting imatinib base to a pharmaceutically acceptable acid addition salt of imatinib base.

2. The process of claim 1, further comprising removing methanol in a continuous or periodical manner while condensing said 3-acetylpyridine with said N,N-dimethylformamide dimethyl acetal.

3. The process of claim 2, further comprising removing methanol in a periodical manner while condensing said 3-acetylpyridine with said N,N-dimethylformamide dimethyl acetal.

4. The process of claim 1, wherein condensing 3-acetylpyridine with N,N-dimethylformamide dimethyl acetal is carried out using between about 1.2 and about 2.0 molar equivalents of N,N-dimethylformamide dimethyl acetal with respect to 3-acetylpyridine.

5. The process of claim 4, wherein condensing 3-acetylpyridine with N,N-dimethylformamide dimethyl acetal is carried out using about 1.5 molar equivalents of N,N-dimethylformamide dimethyl acetal with respect to 3-acetylpyridine.

6. The process of claim 1, wherein reducing N-(5-nitro-2-methylphenyl)-4-(3-pyridinyl)-2-pyrimidineamine using hydrazine in the presence of Raney nickel is carried out using at least a 2 times molar excess of hydrazine with respect to N-(5-nitro-2-methylphenyl)-4-(3-pyridinyl)-2-pyrimidineamine.

7. The process of claim 6, wherein reducing N-(5-nitro-2-methylphenyl)-4-(3-pyridinyl)-2-pyrimidineamine using hydrazine in the presence of Raney nickel is carried out using between about 2 and about 8 molar equivalents of hydrazine with respect to N-(5-nitro-2-methylphenyl)-4-(3-pyridinyl)-2-pyrimidineamine.

8. The process of claim 1, wherein hydrazine is provided in the form of hydrazine hydrate or an aqueous solution of hydrazine hydrate.

9. The process of claim 1, wherein Raney nickel is used in an amount of not less than approximately 10% by weight with respect to N-(5-nitro-2-methylphenyl)-4-(3-pyridinyl)-2-pyrimidineamine.

10. The process of claim 1, wherein reducing said N-(5-nitro-2-methylphenyl)-4-(3-pyridinyl)-2-pyrimidineamine using hydrazine in the presence of Raney nickel is carried out in a $C_1$-$C_4$ alcohol, a $C_1$-$C_4$ aliphatic ether, or a cyclic ether.

11. The process of claim 10, wherein said $C_1$-$C_4$ alcohol is methanol.

12. The process of claim 1, wherein reducing N-(5-nitro-2-methylphenyl)-4-(3-pyridinyl)-2-pyrimidineamine using hydrazine in the presence of Raney nickel to obtain N-(5-amino-2-methylphenyl)-4-(3-pyridinyl)-2-pyrimidine-amine does not also result in the formation of compounds represented by formula 1a and formula 1b:

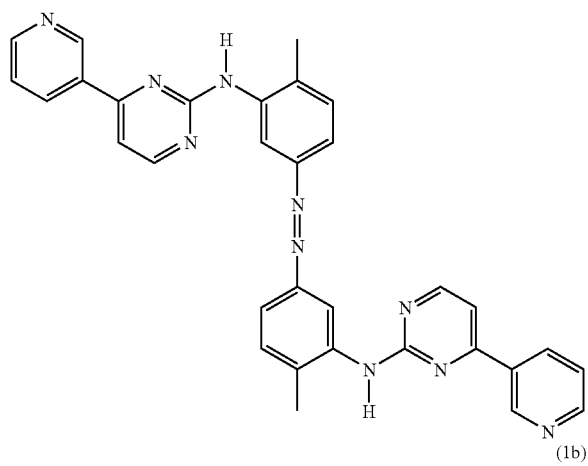

13. The process of claim 1, wherein said inorganic base is potassium carbonate.

14. The process of claim 1, further comprising in (e) adding water and filtering 4-(chloromethyl)-N-(4-methyl-3-(4-(pyridin-3-yl)pyrimidin-2-ylamino)phenyl)benzamide.

15. The process of claim 1, wherein condensing 4-(chloromethyl)-N-(4-methyl-3-(4-(pyridin-3-yl)pyrimidin-2-ylamino)phenyl)benzamide with an excess of N-methylpiperazine is carried out using between about 2 and about 12 molar equivalents of N-methylpiperazine with respect to 4-(chloromethyl)-N-(4-methyl-3-(4-(pyridin-3-yl)pyrimidin-2-ylamino)phenyl)benzamide.

16. The process of claim 15, wherein condensing 4-(chloromethyl)-N-(4-methyl-3-(4-(pyridin-3-yl)pyrimidin-2-ylamino)phenyl)benzamide with an excess of N-methylpiperazine is carried out using between about 5 and about 7 molar equivalents of N-methylpiperazine with respect to 4-(chloromethyl)-N-(4-methyl-3-(4-(pyridin-3-yl)pyrimidin-2-ylamino)phenyl)benzamide.

17. The process of claim 1, further optionally comprising in (f) neutralizing after condensing 4-(chloromethyl)-N-(4-methyl-3-(4-(pyridin-3-yl)pyrimidin-2-ylamino)phenyl)benzamide with an excess of N-methylpiperazine to obtain imatinib base, wherein in (f): the organic solvent is selected from the group of $C_1$-$C_4$ aliphatic alcohols and $C_1$-$C_4$ ketones; and filtering said imatinib base.

18. The process of claim 15, wherein condensing 4-(chloromethyl)-N-(4-methyl-3-(4-(pyridin-3-yl)pyrimidin-2-ylamino)phenyl) with N-methylpiperazine is carried out without an additional solvent.

* * * * *